(12) United States Patent
Canham et al.

(10) Patent No.: US 6,815,360 B1
(45) Date of Patent: Nov. 9, 2004

(54) SILICON MICRO-MACHINED PROJECTION WITH DUCT

(75) Inventors: Leigh T Canham, Malvern (GB); Timothy I Cox, Malvern (GB); Christopher L. Reeves, Malvern (GB)

(73) Assignee: Qinetiq Limited, London (GB)

( * ) Notice: Subject to any disclaimer, the term of this patent is extended or adjusted under 35 U.S.C. 154(b) by 0 days.

(21) Appl. No.: 09/744,152

(22) PCT Filed: Jul. 22, 1999

(86) PCT No.: PCT/GB99/02381
§ 371 (c)(1),
(2), (4) Date: Feb. 8, 2001

(87) PCT Pub. No.: WO00/05166
PCT Pub. Date: Feb. 3, 2000

(30) Foreign Application Priority Data

Jul. 22, 1998 (GB) ............................................. 9815820

(51) Int. Cl.⁷ ...................... H01L 21/302; H01L 21/461
(52) U.S. Cl. ...................... 438/706; 438/719; 438/745; 438/753
(58) Field of Search ................................ 438/689, 706, 438/709, 719, 745, 753

(56) References Cited

U.S. PATENT DOCUMENTS

| 4,969,468 | A | | 11/1990 | Byers et al. |
| 5,137,817 | A | * | 8/1992 | Busta et al. ................. 435/207 |
| 5,262,128 | A | | 11/1993 | Leighton et al. |
| 5,381,753 | A | * | 1/1995 | Okajima et al. ............... 117/12 |
| 5,383,512 | A | | 1/1995 | Jarvis et al. |
| 5,457,041 | A | * | 10/1995 | Ginaven et al. ............. 435/455 |
| 5,591,139 | A | * | 1/1997 | Lin et al. ...................... 604/264 |
| 5,855,801 | A | * | 1/1999 | Lin et al. ........................ 216/2 |
| 6,334,856 | B1 | * | 1/2002 | Allen et al. .................. 604/191 |
| 6,406,638 | B1 | * | 6/2002 | Stoeber et al. ................ 216/11 |

FOREIGN PATENT DOCUMENTS

| WO | WO96/37256 | 11/1996 |
| WO | WO97/04297 | 2/1997 |

OTHER PUBLICATIONS

Caicai Wu et al.: "Oxyhemoglobin measurement of whole blood specimens in a silicon microfabricated cuvette" Micro– and Nanofabricated Electro–Optical Mechanical Systems for Biomedical and Environmental Applications, San Jose, CA, USA, Feb. 1997, vol. 2978, pp. 155–164, Proceedings of the SPIE—The International Society for Optical Engineering, 1997 USA.

* cited by examiner

*Primary Examiner*—Duy-Vu Deo
(74) *Attorney, Agent, or Firm*—Nixon & Vanderhye PC

(57) ABSTRACT

A method of providing a microprojection (180) on the surface of a first material, the microprojection having a base portion adjacent the first material and a remote, or a tip portion, and a duct (182) at least in a region of the tip portion and the method comprising micro-machining the first material to provide the micro-projection duct. Various uses of the microprojection are also disclosed including light guides and cuvettes from micro-analytical systems, microneedles for transdermal fluid delivery or the like.

32 Claims, 9 Drawing Sheets

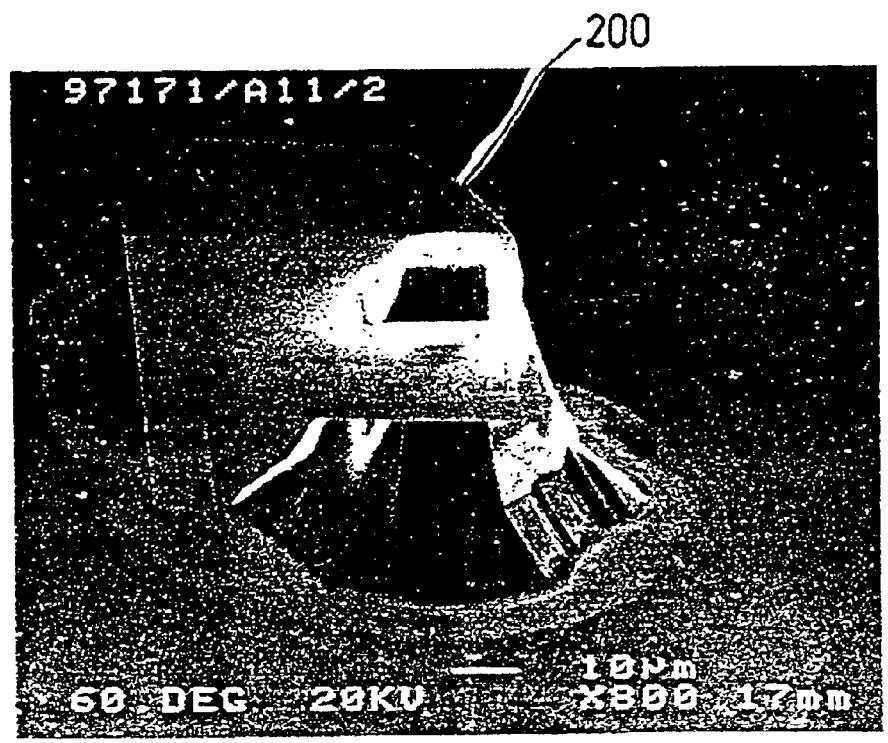
Fig. 14
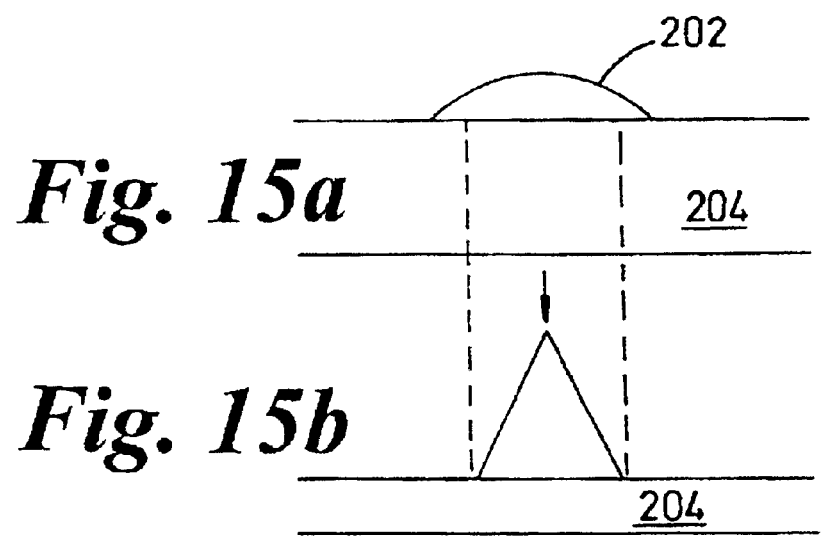
Fig. 15a
Fig. 15b

SILICON MICRO-MACHINED PROJECTION WITH DUCT

This invention relates to providing a novel micro-machined structure and a method for providing the structure.

Micro-machining of silicon (and other materials) to provide structures which have dimensions of the order of micro-meters is known. This technique is used to provide structures fabricated from bulk material and shares some common features with the techniques used to fabricate integrated circuits. For instance it is disclosed in WO 96/10630 to provide tetrahedral structures, or barbs, which have a base dimension of between 30 micro-meters to 80 micro-meters.

It is disclosed in U.S. Pat. No. 5,591,139 to fabricate a microneedle parallel to the surface of a substrate wherein the walls of the needle are fabricated from $SiO_2$ deposited by low pressure chemical vapour deposition. To form such a needle a large number of steps are required.

U.S. Pat. No. 5,262,128 discloses micro-projections having ducts therethrough. It is claimed that the micro-projections may be fabricated by the Liga process. The skilled person will appreciate that this process is not a technique for microstructuring silicon and is used for processing metals and polymeric materials. Further, all structures fabricated by the Liga process must have edges which are substantially perpendicular to the surface of the substrate from which they are formed. From the remainder of this document it will be apparent that the Liga process is not suitable for fabricating the micro-projection disclosed herein.

Further, U.S. Pat. No. 5,262,128 states that the structures disclosed therein were fabricated by techniques well-known in the integrated circuit industry. It is disputed that in 1989, the application date of U.S. Pat. No. 5,262,128, silicon processing techniques, were known which could produce the structures disclosed therein. It is even disputed that such techniques were known in 1993, the publication date of U.S. Pat. No. 5,262,128. Techniques for fabricating high aspect ratio ducts have only recently become known. This is no discussion in U.S. Pat. No. 5,262,128 of how to form the structures shown therein, thus the teachings are not enabling.

An alleged Internet disclosure purportedly dated 22 Jun. 1998 by Georgia Tech (www.gtri/gatech/edu/res-news/needles.htnl) discloses arrays of micro-projections. On the second page of this document it is disclosed that future work includes attempting to fabricate needles which are hollow by some unspecified process. Therefore, the purported Georgia Tech document does not provide an enabling disclosure of hollow micro-projections (since they cannot make them since this is indicated as future work).

Further, the skilled person will appreciate that the fact that other research institutions other than the applicants are working on providing the structures shown in U.S. Pat. No. 5,262,128 points at the non-enabling nature of U.S. Pat. No. 5,262,128.

According to a first aspect of the invention there is provided a method of providing a micro-projection on the surface of a first material, the micro-projection having a base portion adjacent the first material, and a remote, or tip, portion, and a duct at least in a region of the tip portion and the method comprising micro-machining the first material to provide the micro-projection and duct.

The method may comprise forming the duct such that it passes between the tip portion and the base portion.

Indeed, in some embodiments the duct may be formed such that it passes entirely through the micro-projection and may be through the first material supporting the micro-projection. Such a method provides a micro-projection onto the surface of a material through which matter may be passed, possibly a fluid.

The first material may be a semi-conductor, such as silicon material, or other material with a crystal lattice structure. The first material may be glass.

Preferably the base portion has a width of less than approximately 1000 $\mu$m and most preferably less than approximately 100 $\mu$m and possibly below 10 $\mu$m.

The tip portion of the micro-projection may have an apex. The method may fabricate the micro-projection such that the duct is coincident with the apex of the micro-projection. This may provide a needle like structure which has a number of uses.

In one embodiment the method may comprise fabricating the duct in a piece of material and subsequently forming the micro-projection around the duct. If such a method is used the method may comprise fabricating the duct and then fashioning the material such that the tip portion of the micro-projection coincides with the duct. Indeed, the apex of the micro-projection may be fabricated to be coincident with the duct.

The duct may be formed by a number of processes and any one of the following list may be suitable: deep dry etching, laser ablation, light assisted anodisation of n-type silicon in HF acid, focused ion beam milling. Each of these techniques may provide a duct of suitable dimensions for the realisation of the method, and will be known to the person skilled in the art.

A mask layer may be formed on to the surface of the first material. The mask layer may comprise silicon dioxide should the first material be a bulk silicon crystal.

An aperture may be formed into the mask layer using lithographic and etching techniques as will be known to the person skilled in the art.

The first material may be removed from a region underneath the aperture in the mask using an etching technique. This step provides one way of forming the duct.

The duct, or a hole that will become the duct, may be formed in a sheet of planar material. A plurality (e.g. of the order of hundreds of thousands) of ducts may be formed simultaneously.

Once a suitable duct has been formed in, for example, a sheet of material, the micro-projection may be formed from the material by a number of techniques. For example any one of the following list may be suitable: anisotropic wet etching of silicon using liquid alkaline etches, focused ion beam milling, or transferring the pattern to the silicon from a domed resist mask using some form of plasma/ion beam etching.

The mask layer may be removed from the first material. A second masking layer may be created on to the first material which may be silicon dioxide. The second masking layer may be grown (perhaps by a low temperature oxide process LTO) or may be deposited (perhaps by plasma enhanced chemical vapour deposition PECVD). An advantage of removing the first masking layer and creating a second masking layer is that the inside surface of the duct is covered and protected by the second masking layer whereas the first masking layer left this area unprotected. Of course, we may apply the second masking layer without removing the first masking layer (or without removing it completely). The second masking layer may be applied over the hole/duct surfaces.

The second masking layer may be patterned (may be using standard lithographic techniques) and may be subsequently etched.

The second masking layer may be left in the shape of a disc, or a rectangle. In perhaps the preferred embodiment the second masking layer is left with a square remaining. The second masking layer may have its edges aligned with specific crystal planes of the first material. The second masking layer may be silicon dioxide.

In one embodiment the first material (which may be a bulk silicon crystal) may be etched in an anisotropic etch which undercuts the second masking layer. The crystal planes of the first material may have been arranged so that planes having a low etch rate bound the etching process creating the desired micro-projection structure. The second masking layer may then be removed. Such a process results in the micro-projection being formed from the first material.

In an alternative embodiment once the second masking layer has been formed so that it covers the inside surface of the duct, and in this embodiment it also covers the upper surface of the first material, the portion of the masking layer covering the upper surface of the first material may be removed so as to leave the second masking layer covering the inside surface of the duct.

The first material may then be removed from around the masking layer on the inside surface of the duct leaving the masking layer substantially intact. This may result in the micro-projection being formed from the material of the second masking layer (a second material). This may be thought of as fabricating a micro-projection from a second material which is different from that of the first material. The second masking layer may be thought of as the second material.

The second material may substantially completely fill the duct.

In such a case the method may comprise creating a duct in the first material, and lining the duct with the second material. Further steps in the method may be to subsequently remove the first material from around the lining of the second material. Such a method may leave the second material substantially remaining. It may be possible to have the first and second materials the same, if a suitable materials removal technique can be employed, but we prefer to have them different so as to allow their different properties to influence the removal rate of their materials.

In a variation of the method, the second material forms a lining of the duct or hole and a portion of the second material may be removed from the lining of the duct before, or whilst the first material is removed from around the lining. This allows the shape of the resultant micro-projection to be controlled.

The cross section of the micro-projection resulting from such a method may be varied according to the cross section of the duct which was created in the first material.

For instance the cross section may be circular, square, rectangular, elliptical, etc. Each of these cross-sections may be suitable for different applications.

The second material may be $SiO_2$, which is readily formed around a duct should the first material be silicon. The $SiO_2$ layer may be grown by oxidation of the silicon wafer or may be deposited (perhaps by Plasma Enhanced Chemical Vapour Deposition PECVD). Should the second material be a material other than silicon dioxide then the skilled person will appreciate that the second material would need to be deposited (again perhaps by PECVD).

The second material may be metal, or may be another conductor, or may be a ceramic, or may be a polymer. An advantage of using a metal, or a conductor for the second material is that an electrical conductor is produced which would allow currents and potentials to be applied to the micro-projection.

In another embodiment the method may comprise fabricating the micro-projection from the material and subsequently forming the duct through the micro-projection.

To achieve the formation of the micro-projection onto the surface of the first material a masking layer may be created on to the surface of the first material. The masking layer may be in the shape of a disc, or a rectangle. In perhaps the preferred embodiment the masking layer is fabricated as a square. The masking layer may have its edges aligned with specific crystal planes of the first material. The masking layer may be silicon dioxide.

Once the masking layer has been created the first material may be removed from underneath the masking layer by etching using an anisotropic wet etch. In effect, this etch undercuts the masking layer.

The crystal planes of the first material may have been arranged so that planes having a low etch rate bound the etching process creating the desired micro-projection structure. In such a process the anisotropic etch undercuts the masking layer until the slow etch rate crystal planes are met.

Preferably, the duct is fabricated such that the duct is coincident with an apex of the micro-projection.

The micro-projection may be formed by a number of techniques. For example any one of the following list may be suitable: anisotropic wet etching of silicon using liquid alkaline etches, focused ion beam milling, or transferring the pattern to the silicon from a domed resist mask using some form of plasma/ion beam etching.

The method may then comprise covering the micro-projection in a planarising layer. Next, the planarising layer may be etched using a standard lithography to reveal the tip portion of the micro-projection.

Once the tip portion of the micro-projection has been revealed the duct can be etched perhaps by using one of the following techniques: deep dry etching wherein the planarising layer may act as a mask; anodisation of the structure in HF acid; laser ablation; focused ion beam milling. Should anodisation be used it is possible (but it is uncertain) that a coarse tree like pore structure may be produced within the micro-projection. Further, anodisation may be of special benefit for forming small holes with a high aspect ratio. For example holes as small as 1 $\mu$m may be made with an aspect ratio greater than 100 (this is explained in an article by V. Lehmann "The physics of macropore formation in low doped n-type silicon", Journal of Electrochemical Society Vol. 140. October 1993 pages 2836–2843). This is incorporated by reference and the skilled person is directed to read this article.

Once the method has been used to create the micro-projection and duct the method may further include linking the duct to a reservoir to create a device.

The first step in such a process may be to ensure that the duct passes entirely through the material being processed, ensuring that the remaining steps are easier to perform.

One possible way of doing this is to ensure that the duct is long enough to pass through the material. Alternatively, or additionally, matter may be removed from a side opposite a side of the first material where the micro-projection has been fabricated. Both of these techniques ensure that the duct passes completely through the material.

Next, the material may be attached to a piece of a second material. The second piece of material may have a channel which when the two pieces of material are attached connects to the duct and may link the duct to a reservoir.

The channel may be cut into an upper surface of the second piece of material, so providing a channel which may be easy to fabricate.

Alternatively, or additionally, a channel may be cut into a rear face of the first material.

The first and second materials may be the same material. Preferably, the two materials are silicon, preferably a hulk silicon single crystal. Alternatively, the first or the second material may be glass.

It is possible to bond glass to silicon using anodic bonding and it is also possible to etch channels in to glass.

In a further step of the method the surface of the materials (perhaps the first material, or perhaps the second material) may be modified. In one particular embodiment the surface of the first material may be porosified, so modifying the material's interaction with biological systems. This is explained in an article by L. T. Canham—"Bioactive silicon structure fabrication through nanoetching techniques": Advanced Materials volume 7 page 1033 (1995). This is incorporated by reference and the skilled person is directed to read this article.

Such porosification may be performed by electrochemical anodisations processes (may be in HF acid) or possibly by immersing the structure into a stain etching solution.

The stain etching solution may be a mixture of hydrofluoric acid and nitric acid. This mixture is especially suitable for etching silicon.

The shape of the micro-projection may be altered by subsequent processing. For instance part of the micro-projection may be cut away. This cutting may be performed using ion beam etching or other similar processes.

Preferably the micro-projection has an axis which is substantially normal to the surface of the first material. Alternatively, an axis of the micro-projection may be inclined at an angle to the surface of the first material.

According to a second aspect of the invention there is provided a micro-projection having a base portion which is provided on the surface of a first material, and a remote or tip portion, wherein the micro-projection has a duct in at least a region of the tip portion.

The duct may pass between the tip portion and the base portion. Indeed, the duct may pass entirely through the micro-projection.

Alternatively, the duct may be provided as an indentation in a region of the tip portion of the micro-projection. This may be advantageous in that it would allow matter, perhaps a liquid, to be held in the indentation.

The micro-projection may be a micro-needle or may be a micro-barb. Alternatively, the micro-projection may be thought of as a micro-tube.

The micro-tube/micro-projection may be fabricated in a sheet of silicon or other semiconductor material, or indeed other crystal lattice material.

The base portion has a width of less than approximately 1 mm and preferably less than approximately 100 $\mu$m, and may be less than approximately 10 $\mu$m.

Preferably the micro-projection is transverse to the surface of the first material, and most preferably normal to it. This may make the micro-projection easier to fabricate and involve less processing steps than prior art techniques. Further, fabricating a micro-projection normal to the surface may allow an array of projections to be formed. It may be easier to connect the micro-barb to a channel. The micro-projection may of course be fabricated at an angle to the surface of the first material.

The micro-projection may be fabricated from the first material. This may make the micro-projection mechanically stronger than if the micro-projection were fabricated from another material.

There may be an array of micro-projections extending away from a common carrier, preferably extending perpendicular to the plane of a substrate sheet. The micro-projections may share a common reservoir. The common carrier may be the first material.

The micro-projections may have a length of up to substantially 2 mm. Alternatively, the micro-projection may have a length of up to substantially up to 500 $\mu$m. In one embodiment the micro-projection may have a length substantially in the range 0 to 300 $\mu$m.

The base portion of the micro-projections may be up to substantially 1 mm in width. Alternatively the base portion of the micro-projection may have a width of substantially 50 $\mu$m or may have a width of substantially 10 $\mu$m or may be 5 $\mu$m.

The skilled person will appreciate that the dimensions of the micro-projection may be limited by the technique used to form the projection. That is the available aspect ratio of the fabrication technique may be the limiting factor.

A high aspect ratio dry etching process may be used to form the duct. Alternatively, or additionally, the duct of the micro-projection may be formed by the fabrication of porous silicon.

Should the method discussed hereinbefore, wherein a second material is used to line a duct, or hole, in a first material followed by subsequent removal of the first material, the duct may have dimensions substantially in the range of 200 $\mu$m length, may be with a width of substantially 10 $\mu$m.

There may be up to substantially 2500 micro-projections provided on a 5 mm square piece of material. Of course, the skilled person will appreciate that the number of micro-projections which it is possible to provide within a 5 mm square of material depends on the size of the micro-projections. The number quoted is a guide to the number which may be achieved and represents a realistic number.

The skilled person will realise that the dimensions of the micro-projections can be altered to suit the application by altering the fabrication parameters used to create the micro-projections.

The method may comprise using an array of micro-projections with the duct of each micro-projection being connected to a single reservoir.

In one embodiment the surface of the micro-projections may be porosified. An advantage of this is that the bioactivity of the surface may be controlled; especially should the first material be silicon. This is advantageous in some applications, for instance should the micro-projections be used in transdermal drug delivery. (By bio-active it is meant that the material induces a specific biological process. For example, it may induce calcium phosphate precipitation within living systems).

The needle may become bio-compatible because of the porosification. This is advantageous because if the needle breaks when being used to pierce a user's skin it may be resorbed by the body reducing problems associated with the broken needle.

According to a third aspect of the invention, there is provided a micro-tube fabricated in the surface of a first material.

Preferably the micro-tube has a base portion with a width of less than approximately 1mm and more preferably less than approximately 100 $\mu$m and possibly below 10 $\mu$m.

The micro-tube may be fabricated from a substance other than that of the first material. In one embodiment the first material may be silicon and the micro-tube may be fabricated from $SiO_2$. Of course, other possible combinations of materials are possible. For instance metals, ceramics, or polymers may be used from which to form the micro-tube.

The micro-tube may have a cross-section that is substantially circular, possibly substantially square, possibly elliptical, possibly rectangular.

The micro-tube may comprise a micro-cuvette.

The micro-tube may be filled with a filler material. The filler material may be a different material to wall portions of the micro-tube or alternatively, the filler material may be the same material as the wall portions of the micro-tube. Indeed, the micro-tube may be thought of as a solid micro-projection, or micro-rod.

According to a fourth aspect of the invention there is provided a micro-analysis system in which a micro-tube according to the third aspect of the invention is provided and in which an analysis means is provided to analyse a substance within the micro-tube.

Such a system could prove beneficial in that it would allow samples to be analysed in a confined spaces. A fabricated micro-tube may be transparent to IR, UV and possibly visible light and, as such, would allow "on chip" spectroscopy. That is spectroscopy within a system provided on a single chip or package.

The micro-analysis system could comprise more than one micro-tube and may possibly comprise an array of micro-tubes. Such an arrangement would allow more samples to be tested or allow a variety of samples to be tested at the same time. The micro-tubes may comprise micro-cuvettes.

Providing an array of micro-tubes is advantageous in that it would allow many samples to be tested at the same time.

The micro-analysis system may be combined with a micro-tube array acting as a micro-pipette array.

The micro-analysis system may comprise a delivery system so allowing chemicals, or other substance to be tested, to be inserted into the micro-tube.

The delivery system may comprise a micro-pipette or may comprise a duct fabricated into the first material, or may comprise an array of micro-pipettes or ducts.

The analysis means may comprise a light source, adapted to shine light through the micro-tube and a detector to detect light passing through the micro-tube or to detect the fluorescence generated by the incident light. This may provide a suitable way of analysing the contents of the micro-tube.

The light source may be an LED or may be a LASER. The light source (or the detector) may further comprise filters and may have beam shapers, lenses, etc. to ensure light having the desired properties passes through the micro-tube.

Such optical components may be fabricated using the same wafer of first material from which the micro-tube is fabricated. This is particularly advantageous should the micro-analysis system be reusable. This would make the process of fabricating the single wafer device more cost effective.

According to a fifth aspect of the invention there is provided a micro-manipulation system using the structure of the third aspect of the invention wherein the micro-tube is connected to a pump.

The pump may be a vacuum pump.

Such an apparatus may prove beneficial in that it would allow small objects to be picked up by the micro-tube.

The micro-tube may be connected to the pump via a duct in the material. This provides a simple structure.

Control electronics may be provided on the first material which controls how the device operates. Such a structure may lead to an integrated package, containing both the control electronics and the micro-manipulation system.

Alternatively, or additionally, microfluidic pumps, and/or micro-fluidic valves may also be provided on the first material. Such devices are advantageous because they allow the fluids within the micro-manipulation system to be pumped to different points as required. The micro-fluidic pumps may comprise a heating element. The heating element may be a resistor.

According to a sixth aspect of the invention there is provided a method of coupling an optical fibre to the first material comprising providing a micro-tube according to the third aspect of the invention and using the micro-tube as an optical coupling component.

Preferably the optical coupling comprises a wave guide. The wave guide may be a micro-tube or may be a micro-rod.

Optical may be intended to cover any electromagnetic wave, for instance radio, visible light, ultra violet, infra-red, etc.

Such a structure may provide a simple way of coupling the optical fibre to the material. It has the advantage over conventional techniques in that the fibre may be connected normal to the material as opposed to having to be orthogonal to the material.

According to a seventh aspect of the invention there is provided an optical coupling system adapted to couple an optical fibre to a substrate, the coupling system comprising a micro-tube fabricated on the surface of the substrate.

The optical fibre may be inserted into the micro-tube to achieve efficient coupling.

According to an eighth aspect of the invention there is provided a method of optically connecting two wafers of material together comprising providing on a first of the wafers a micro-tube according to the third aspect of the invention and coupling this to the second wafer in such a way so as to enable light to be passed between the two wafers.

This may allow signals, which may be optical signals, to be passed between the two wafers with low losses.

The method may comprise ensuring that light being transmitted passes entirely through wave guides (i.e. does not travel through free space). This has the advantage, over free space interconnection schemes, that dust and other such debris does not degrade the quality of the signal.

According to a ninth aspect of the invention there is provided a structure for optically connecting two wafers of material, the structure comprising a micro-tube fabricated on to the first wafer and being connected to the second wafer.

According to a tenth aspect of the invention there is provided an array of micro-projections.

There may be provided an array of micro-needles. Indeed, there may be provided an array of micro-tubes.

According to a eleventh aspect of the invention there is provided a micro-barb on the surface of a material having a base portion adjacent the first material in which the barb has a porosified surface.

Preferably the base portion has a width of less than approximately 1000 $\mu$m and most preferably less than approximately 100 $\mu$m and possibly below 10 $\mu$m.

The barb may be formed by the processes described in relation to the first aspect of the invention.

The porosification may be performed by electrochemical anodisations processes (possibly in HF acid or possibly by immersing the structure into a stain etching solution). Possibly the stain etching solution is a mixture of hydrofluoric acid and nitric acid.

There will now be described, by way of example only, embodiments of the present invention with reference to the accompanying drawings, of which:

FIG. 14 shows a photograph of a scanning electron microscope image of a further micro-projection fabricated according to the invention;

FIGS. 15A-15B shows the use of a domed resist mask to fabricate a micro-projection;

Figure 1A:
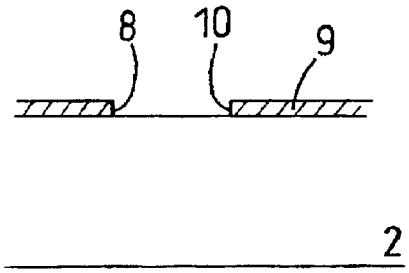
FIGS. 1A-1F shows schematically various stages in a first part of a process for the manufacture of a barb or microneedle according to the present invention.

FIG. 1 shows a wafer of bulk silicon 2, typically single crystal silicon, on which there are performed various processes which form a duct 4 before the structure of a micro-projection 6 is formed.

The first step in the process is to define the edges 8, 10 of the duct using a suitable masking layer and standard lithography and etching techniques. In this example a 650 nm thick silicon dioxide layer 9 was grown on the wafer by wet oxidation at 1000° C. for 160 minutes. HPR-505 photoresist was then spun on to the wafer at 4200 rpm. This gives a resist thickness of 1.55 microns. The photoresist is then soft baked at 120° C. for 45 seconds. The photoresist is then patterned using a Süss mask aligner. The photoresist is then developed using the procedure specified for that resist. The photoresist is then hard baked at 105° C. for 45 seconds.

The wafer is then placed in 5:1 buffered hydrofluoric (5 parts ammonium fluoride to 1 part 40 wt % HF solution) until the wafers run clear, i.e. the surface is rendered hydrophobic. This takes approximately 5 minutes. The resist mask is left in place for the deep dry etching process.

Figure 1B:
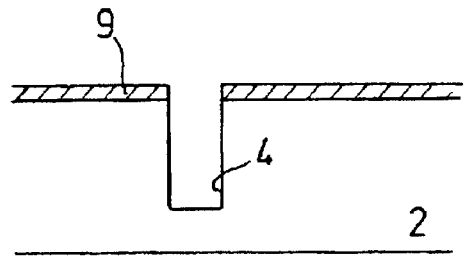
Figure 1C:
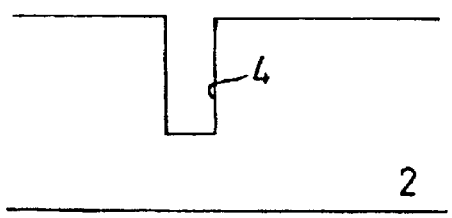

Holes are etched to a depth of approximately 100 microns forming the ducts 4 in an STS deep dry etcher using a timed etch of 35 minutes. This uses a proprietary plasma etching process using a two step process which is continuously repeated. The step of forming the ducts is shown in FIG. 1b wherein the resist mask and the silicon dioxide protect the silicon wafer.

Figure 1D:
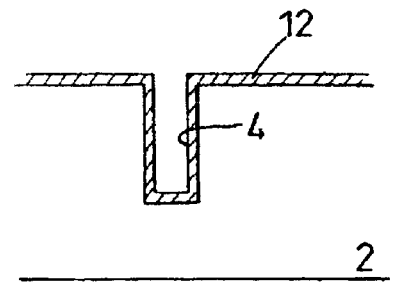

The $SiO_2$ layer is then removed using hydrofluoric acid (FIG. 1c) and a further layer of 650 nm thick silicon dioxide 12 is grown onto the surface of the wafer (FIG. 1d). (The skilled person will appreciate that the $SiO_2$ layer will also grow on a rear surface of the wafer). The growth of the oxide layer can be achieved using the process as outlined above.

Then a lithography process and subsequent etching process is used to mask the $SiO_2$ layer with photoresist such that an amount of $SiO_2$ is left forming a square around each duct 4. It would be possible to use the wet masking and etching process outlined above to pattern the $SiO_2$(12) but it is preferred to use a dry etching process so that leakage of the liquid etchant in to the duct 4 is avoided.

The silicon wafer is then etched using wet etching of the silicon in potassium hydroxide (in this case 30 g of KOH per 100 ml of solution at 90° C. for 20 minutes). Other etchings would also be possible and an example would be an aqueous solution of tetraethyl ammonium hydroxide. The use of potassium hydroxide is preferred since it provides the desired etch dependence on the orientation of the crystal planes in the silicon. However, the use of tetra methyl ammonium hydroxide (TAM) may also be possible should the relatively low selectivity of etch rates between silicon and silicon dioxide in potassium hydroxide be a problem. A 6% aqueous solution of TAM may be suitable.

Figure 1E:
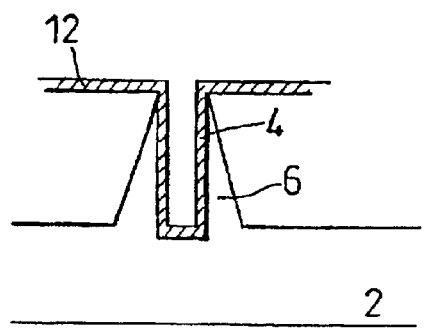

This etch relies on the fact that different crystal planes etch at different rates. Thus when a plane with a low etch rate is exposed the etch stops on that surface. The final structure is then bounded by those planes which have a low etch rate. It is then possible to arrange the orientation of the starting material and that of the etch mask to produce needles with high aspect ratios and sharp tips. The mask usually used for this process is $SiO_2$ which is produced in the high temperature oxidation of the silicon as described above. The oxidation step also conveniently produces a layer of $SiO_2$ on the inside of the ducts which serves to protect the duct during the subsequent wet etching stage. Thus the micro-projection structure is formed (FIG. 1e).

However, it would also be possible to provide layers(12) using deposition process, rather that the thermal oxidation of silicon. It would be necessary to ensure that a process was used with a good step coverage, for example Chemical Vapour Deposition (CVO).

Once a sufficient amount of the silicon has been etched the process is stopped and the remaining $SiO_2$ mask(12) is removed by etching in HF acid. This leaves the structure shown in FIG. 1f. The structure shown in FIG. 14 has a plane of mask 200 left attached to a top portion of the micro-projection and represents the structure shown in FIG. 1e. This mask 200 can be readily removed using an HF acid solution which etches the mask but not the micro-projection.

The skilled person will realise that there are variations to the above process which can be used, For instance the duct can be formed into the silicon using a number of different processes including: laser ablation (this is a serial technique wherein holes as small as 1 micron can be defined with the limit of the aspect ratio (depth to width) of about 10:1); light assisted anodisation of low doped (possible with a resistivity substantially in the range 1–500 Ωcm) n-type silicon (a parallel technique wherein an array of ducts is formed each duct being substantially in the range 0.1 micron to 20 microns, with the spacing between the ducts of the same order. Aspect ratios of substantially 100:1 are obtainable). However, as will be appreciated the mark to space ratio (i.e. spacing between holes: hole diameter) is also important for this technique and may be limited to substantially 10:1. Anodisation of n-type silicon is described in an article by V.

Lehmann, "The physics of macropore formation in low doped n-type silicon" in The Journal of the Electrochemical Society (1993) vol. 140 pp2836–2843. This paper is incorporated by reference and the skilled person is directed to read the paper. Focused ion beam milling could also be used, which is a serial technique wherein the channels produced can be as small as substantially 1 micron with an aspect ratio of substantially 10:1.

Also, the shape of the micro-projection could be formed in a variety of ways. For instance focused ion beam milling could be used wherein no mask layer is used and the material is directly milled away using a fine focused ion beam which is scanned around the surface.

In yet another alternative, the pattern may be transferred to the silicon using a domed resist mask using some form of plasma/ion beam etching which has high selectivity between the mask and the silicon such that the silicon etches at a much higher rate than the masking layer. This is carefully controlled to amplify the domed shaped mask in the underlying etched layer. The domed resist shape is produced for example either by flowing a resist image by heating or by the use of grey scale lithography. (The domed resist shape has been used to fabricate micro lenses: M. McCormick, large area full fill factor micro-lens arrays, IEE colloquium on micro engineering applications in optoelectronics vol. (1996) p 10/1–10/3). This paper is incorporated by reference and the skilled person is directed to read the paper.

The principle of using the domed resist mask is shown in FIGS. 15a and b wherein the FIG. 15a shows the initial mask shape 202 is formed onto a wafer 204 and FIG. 15b shows how the final structure relates to the initial mask.

In an alternative approach to fabricating the micro-projection according to the present invention the outer surface of the barb can be fabricated before the duct is formed in the wafer. A possible process for performing this route is shown in FIG. 2. The structure of the barb 20 has been formed and is shown in FIG. 2a on top of a wafer of silicon 19. Processes suitable for this are outlined in relation to FIG. 1 above and include: anisotropic wet etching, focused ion beam milling or using a domed resist mask.

In the preferred embodiment the specific process details are the same as those described in relation to FIG. 1. It will be realised that there is no need to fabricate the duct before the projection is formed.

As the process described in relation to FIG. 1 once the masking layer has been formed the silicon wafer is again etched. Again the preferred etch uses potassium hydroxide solution. This etch relies on the fact that different crystal planes etch at different rates. Thus, when a plane with a low etch rate is exposed the etch stops on that surface. The final structure is then bounded by those planes which have a low etch rate. It is then possible to arrange the orientation of the starting material and that of the etch mask to produce needles with high aspect ratios and sharp tips. Thus the micro-projection structure is formed as shown in FIG. 2a. The specific details of forming sharp barbs is described in a paper: H. L. Offereins, K Kuhl, H Sandmaier, Methods for fabrication of convex corners in anisotropic etching of <100> silicon in aqueous KOH published in Sensors and Actuators (1991), volume 25–27, page 9–13. This paper is incorporated by reference and the skilled person is directed to read the paper.

Once the micro-projection structure has been formed the duct must be formed through a central portion. To achieve this the micro-projection 20 must be protected with a mask so as to just expose the apex of the micro-projection 20. The skilled person will realise that lithography process used for making a mask are generally performed on a planar surface. Since the tip of the micro-projection 20 is not planar it must be planarised before the mask can be created.

Figure 2A:
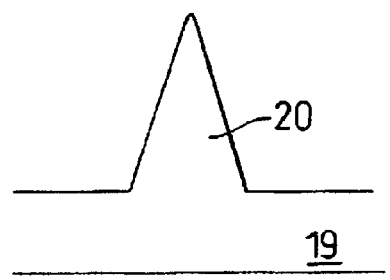
FIGS. 2A-2F shows schematically various stages in a first part of an alternative process to that shown in FIG. 1 for the manufacture of a micro-projection according to the present invention.
Figure 2B:
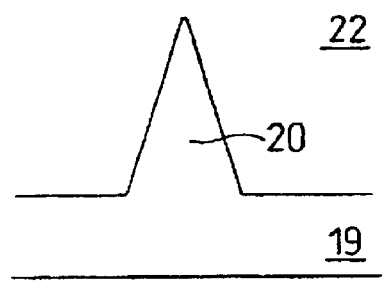
Figure 2C:
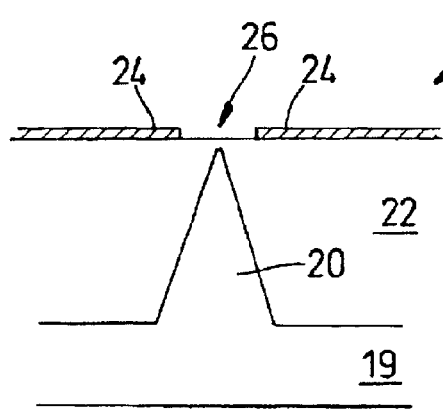
Figure 2D:
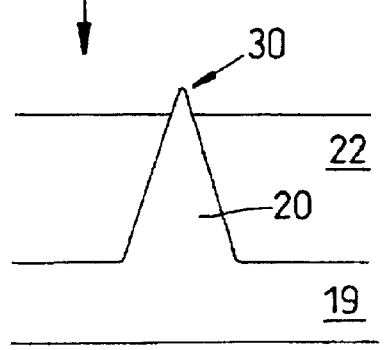

One way of achieving this is as follows. Lay down a planarising layer 22 which in one embodiment is a organic polymer spun onto the wafer covering the micro-projection 20 as shown in FIG. 2b. Once the planarising layer 22 has been deposited there are then two possible routes. The first of these routes is shown in FIG. 2c in which standard lithography is carried out on top of the planarising layer wherein a layer of photoresist 24 is provided and subsequent lithographic steps are carried out. The layer of photoresist 24 may be formed using the steps of i) spinning on layer of photoresist, ii). developing photoresist, which removes areas of either exposed or unexposed photoresist depending on the type of photoresist. This provides the structure of FIG. 2c in which there is a gap 26 in the mask 24 above the apex of the micro-projection 20.

Figure 2E:
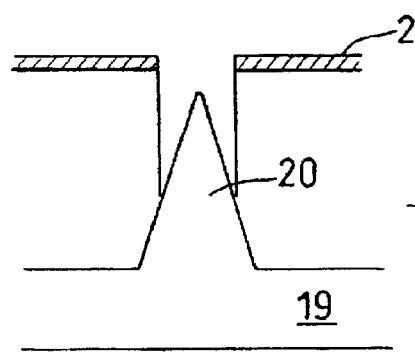

The planarising layer 22 is then etched by a dry etching steps using the photoresist 24 as a mask and this is represented in FIG. 2e.

Figure 2F:
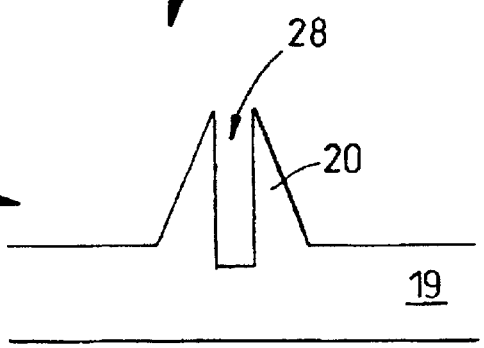

A duct 28 can then be etched into the micro-projection 20 using deep dry etching or anodisation of the structure to arrive at the desired structure as shown in FIG. 2f. A deep dry etching process would be similar to the process described hereinbefore and the anodisation process described in the above Lehmann reference would be used.

In anodisation of the structure the mask must be able to withstand the light assisted anodisation solution which may be a few percent aqueous hydrofluoric acid (typically 4% aqueous HF). In such a process it is possible that a coarse tree like pore structure will be produced within the needle. For such a process to work the mark space ratio between the duct diameter and the duct spacing should be less than 10. The duct radius may be limited to substantially the range 0.2 $\mu$m to 20 $\mu$m.

In an alternative way of arriving at the desired structure the planarising layer 22 can itself be used as a mask layer wherein the structure of FIG. 2b is etched so that the tip of the micro-projection 20 is exposed as at position 30. The duct 28 can then be etched into the micro-projection 20 as described hereinbefore such that the cross section of the duct corresponds to the maximum cross section of the portion of the exposed micro-projection.

Alternatively, it may be possible to drill the duct directly into the micro-projection using either laser ablation or focused ion beam milling. This would obviate the need for either a planarising layer or the performance of any lithography.

Figure 16:
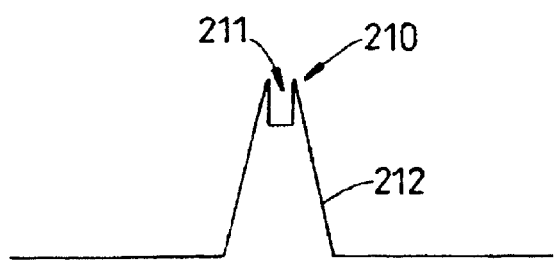
FIG. 16 shows a possible further embodiment of a micro-projection fabricated according to the invention.

The processes described in relation to FIGS. 1 and 2 could be used to fabricate the structure shown in FIG. 16, wherein a duct 211 has been fabricated in a region of an apex 210 of the barb 212. The skilled person will appreciate that using the processes so described will allow the duct 211 to be fabricated to any depth from only in the region of the apex (as shown in FIG. 16) to completely through the first material.

Figure 1F:
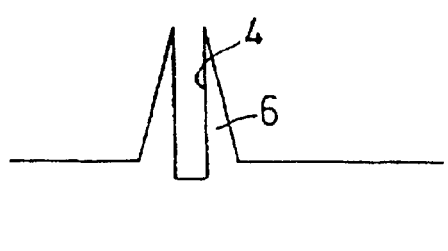

Once the structures of FIGS. 1f and 2f have been produced in some embodiments further processing steps can be performed and such further processing steps are described with the aid of FIG. 3.

Figure 3A:
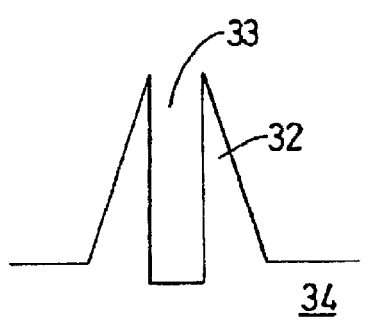
FIGS. 3A-3C shows schematically various stages in a second part of a process for the manufacture of a micro-projection according to the present invention.
Figure 3B:
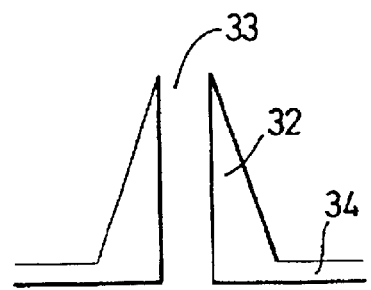

FIG. 3a shows a barb 32 with a duct 33 passing through a central portion attached to a wafer of silicon 34 as is shown in FIGS. 1f and 2f. FIG. 3b also shows this except that the wafer 34 has been thinned below the micro-projection 32 so that the duct 33 passes entirely through the wafer 34. An alternative to thinning the wafer 34 would be to ensure that when the duct 33 is fabricated (as described with reference to FIGS. 1 and 2) that the duct 33 is long enough to pass entirely through the wafer 34.

Figure 3C:
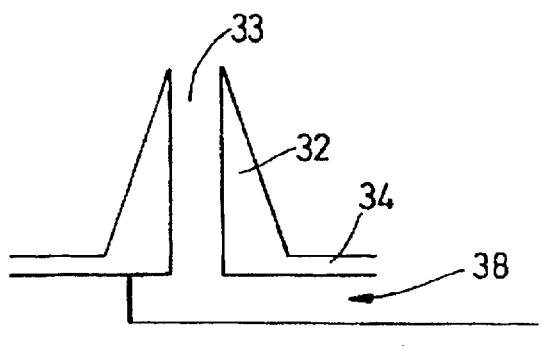

In FIG. 3c a second wafer (or handle wafer) of silicon 36 having a channel 38 etched into the surface (the processes for making a channel 38 in the surface of a wafer 36 will be evident to the person skilled in the art) is attached to the under side of the first wafer 34 so that the channel 38 communicates with the duct 33 passing through the micro-projection 32. Of course, the channel 38 could also be etched onto the rear surface of the first wafer 34 to communicate with the duct 33 passing through the micro-projection 32 and second wafer having a planar face brought into contact with the first wafer 34. Of course, the first and second wafers could both have channels etched onto them.

The skilled person will know of suitable techniques for joining the two wafers together but suitable examples may be by the use of adhesive or use of wafer bonding.

In use, material can be forced along the channel 38, along the duct 33 passing through the micro-projection before being expelled from the apex of the micro-projection 32. Further, the duct 38 may be connected to a reservoir, etc.

All or part of the surfaces within the final structure may be treated in such a way as to modify their interaction with biological systems. This might be achieved by forming a layer or porous silicon (possibly by electrochemical anodisation or possibly by immersing in a stain etching solution such as a mixture of hydrofluoric and nitric acid.) This may for example stimulate the growth of hydroxyapatite in body fluids.

FIG. 4 shows an alternative method for making a micro-projection according to the present invention. The steps represented by FIGS. 4a to 4c are the same as those explained in relation to FIGS. 1a to 1d. That is a silicon dioxide layer 40 is created by thermal oxidation of the silicon wafer 42. An aperture 41 is created in the oxide layer 40 using lithography and etching techniques. This results in the structure of FIG. 4a.

Figure 4A:
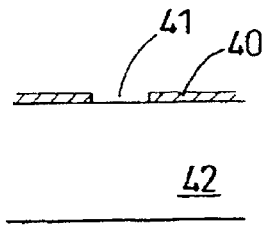
FIGS. 4A-4E shows schematically various stages in an alternative process for the manufacture of a micro-projection according to the present invention.
Figure 4B:
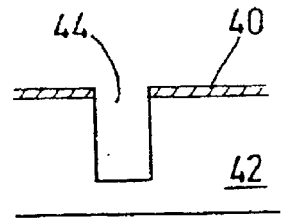
Figure 4C:
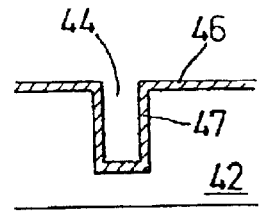
Figure 4D:
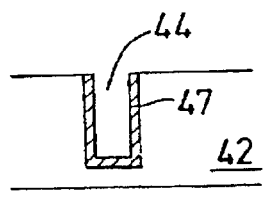

A duct 44 is then etched into the silicon wafer using an appropriate etching process (FIG. 4b). In this case a plasma based etching system (STS) was used to produce a square duct of cross section 20 microns to a depth of 100 microns. Other possible techniques for creating the duct could be laser ablation, or focused ion beam etching or light assisted anodisation of silicon.

The silicon dioxide layer 40 is removed and a new oxide layer 46 is created by heating the silicon wafer 42 for a suitable amount of time at an elevated temperature in oxygen. Alternatively materials could also be deposited using electroplating from a solution or deposition by a gas phase technique such as Plasma Enhanced Chemical Vapour Deposition (PECVD), or Low Pressure Chemical Vapour Deposition (LPCVD). (It would also be possible to provide a new layer from a material other than an oxide for example a metal layer, or a ceramic layer.) The new oxide (or other) layer covers both the original surface of the wafer and the surface of the duct 44, as represented by the reference numeral 47.

The skilled person will appreciate that sufficient oxide (or other material) could be deposited or grown in this process so that the inside of the duct 44 is completely filled with the new material (second material). This would result in a solid micro-projection fabricated from a second material being formed on the surface of the first material.

It is from this point that the process represented by FIG. 4 differs from that shown in relation to FIG. 1. The oxide layer 46 is now removed from the surface of the silicon wafer 42 leaving only the region of the oxide layer 47 inside the duct 44 remaining as shown in FIG. 4d. To achieve this a masking layer is placed over the top of the duct 44 to protect the region of the oxide layer 47 within the duct 44 from being removed. The layer of oxide (or other material) 46 can be removed using usual etchings capable of removing $SiO_2$. (For instance HF acid or plasma based etching processes can be used).

Figure 4E:
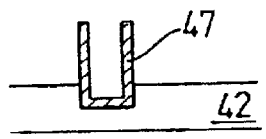
Figure 6:
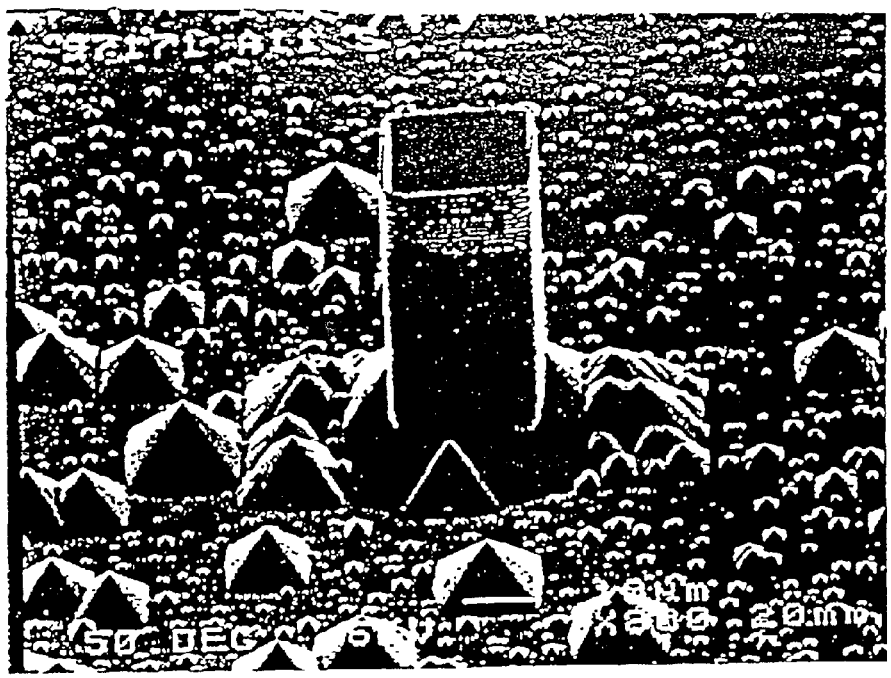
FIG. 6 shows a photograph of an electron microscope image of a micro-projection according to the present invention.

Once the region 46 of $SiO_2$ has been removed leaving the region 47 of the oxide layer remaining the silicon wafer is etched, using an etchant which attacks the silicon but leaves $SiO_2$ (or layer of other material) intact, in this case a solution of tetramethyl ammonium hydroxide. This leaves the $SiO_2$ layer 47 which was previously lining the duct 44 remaining. A photograph from a scanning electron microscope of the structure shown in FIG. 4e is shown in FIG. 6. Analysis of the silicon dioxide tube using Energy Dispersive X-ray analysis (EDX) shows that the material is silicon dioxide with the carbon level below the detection limit for this technique (that is less than about 5 atomic percent).

The skilled person will realise that it would be possible to coat the inside of the duct 44 with a material other than $SiO_2$ in which case the final structure of FIG. 4e and FIG. 6 would be of that material. For instance various metals or possibly ceramics or possibly a plastics material or a polymer could be used.

Figure 5A:
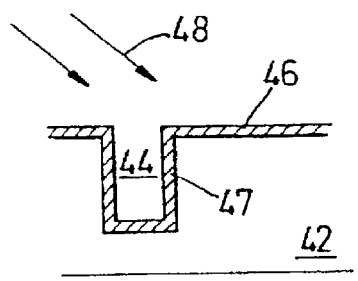
FIGS. 5A-5C shows schematically various stages in a variation of the process shown in FIG. 4.
Figure 5B:
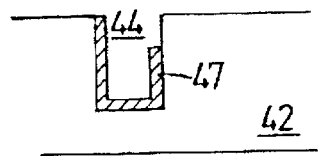
Figure 5C:
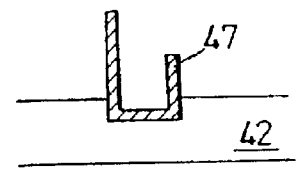

A variation of the process shown in FIG. 4 is shown in FIG. 5. The steps of FIGS. 4a to 4c remain unchanged and the resulting structure is shown in FIG. 5a. The oxide layer 46 can be removed using an ion beam 48 incident at an angle which is not normal to the surface of the silicon wafer 42. In this case, the ion beam used was an argon ion beam having an energy of 500 eV at an angle of 45° to the normal with a beam current of 0.2 mAcm$^2$ and a duration of 40 minutes. As can be seen in FIG. 5b, due to the angle of incidence of the ion beam, part of the oxide layer 47 within the duct 44 is removed. That is, the structure of the wafer shields the remaining region from the ion beam 48.

The silicon wafer 42 is then etched with a suitable etchant which gain leaves the $SiO_2$ layer intact. In this case tetramethyl ammonium hydroxide was again used. A photograph of a scanning electron microscope image of the structure of FIG. 5c can be seen in FIG. 7. The process described in relation to FIG. 5 could perhaps be used to provide a way of providing an angled portion for micro-projections similar to those shown in FIGS. 4e and 6.

The skilled person will realise that had a round cross section of micro-projection been used the final structure would have a round cross section. If the micro-projection had a portion removed as in FIGS. 6 and 7 then the final structure has a bevelled end portion. Such a profile might be useful if the micro-projection was to be used as a needle for the injection of material, for example as part of a transdermal drug delivery system.

Figure 17:
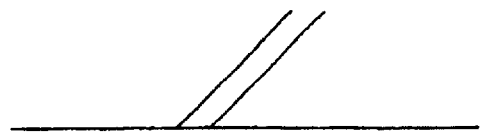
FIG. 17 shows yet another possible embodiment of a micro-projection fabricated according to the invention.

The processes described in FIGS. 4 and 5 could be used to fabricate a micro-projection which is inclined at an angle to the surface of the first material and such a structure is shown in FIG. 17. The skilled person will appreciate that by fabricating the initial duct 44 in the processes of FIGS. 4 and 5 at an angle will allow the final micro-projection to be fabricated at that angle. The processes of FIGS. 1 and 2 may also be used to fabricate micro-projections which are inclined at an angle to the surface of the first material. This could only be achieved using focused ion beams of laser ablation to perform the etch. The remaining techniques mentioned herein are only suitable for providing structures normal to a surface.

Figure 7:
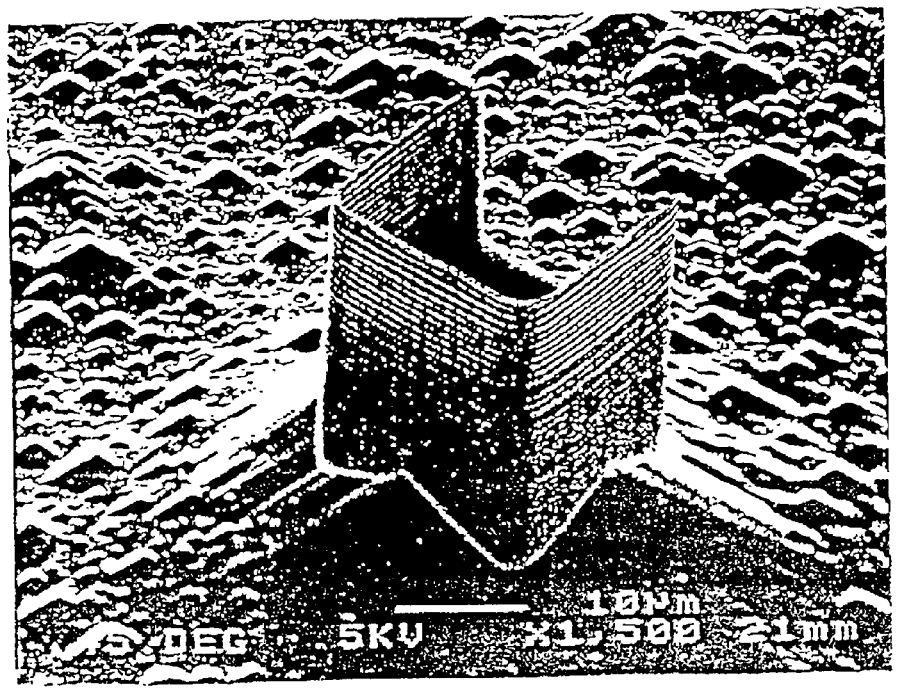
FIG. 7 shows a photograph of an electron microscope image of an alternative micro-projection to that shown in FIG. 6.

Some possible uses of the ducts of FIGS. 6 and 7 are shown in FIGS. 8 to 11.

Figure 9:
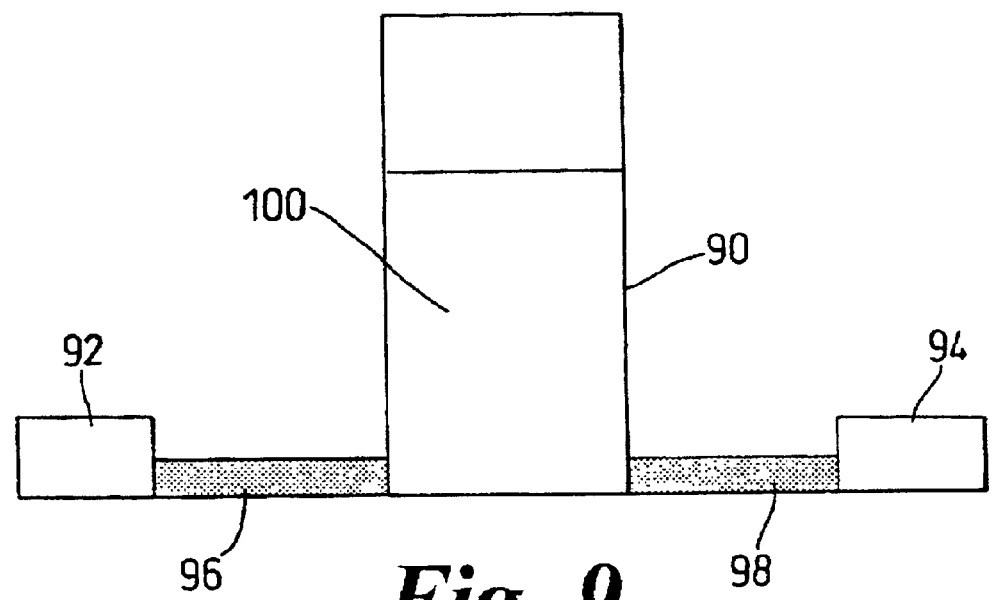
FIG. 9 shows a cross section through a micro-analysis system according to the present invention.

FIG. 9 shows the micro-projection 90 (in this case referred to as a micro-tube 90) of FIG. 6 being used as part of a micro-analysis system which could also be integrated with control circuits. The micro-tube 90 is fabricated on top of a silicon wafer as described hereinbefore. Also provided on the wafer are a light source 92, a detector 94 and two waveguides 96, 98. The first wave-guide 96 guides light emitted from the light source 92 to the cuvette 90 and the second wave-guide 98 guides light which has passed through the micro-tube 90 to the detector 94.

In use, a sample to be tested could be placed into the micro-tube 90 as represented by the reference numeral 100. This material could be chemical or bio-chemical and could be placed into and removed from the micro-tube 90 chambers via a separate micropipette array or perhaps via an on-chip microfluidic chemical delivery system.

The detector 94 can be used to measure the amount of light absorbed by the material in the cuvette 90 or how the amount of light absorbed changes as a reaction proceeds.

It would also be possible to provide materials which fluoresce when light is incident upon that material within the cuvette 90 and to measure the amount of fluorescence from that material when a light beam is incident upon the cuvette 90. In such a situation it would be possible to provide the sensor detecting the amount of fluorescence at an angle to the incident beam. Perhaps the sensor may be substantially at right angles to the incident beam.

The cuvette 90 may be a micro-reactor, for example the cuvette 90 may be a polymeraise chain reactor (PCR) as part of a DNA amplification and analysis system.

Figure 8:
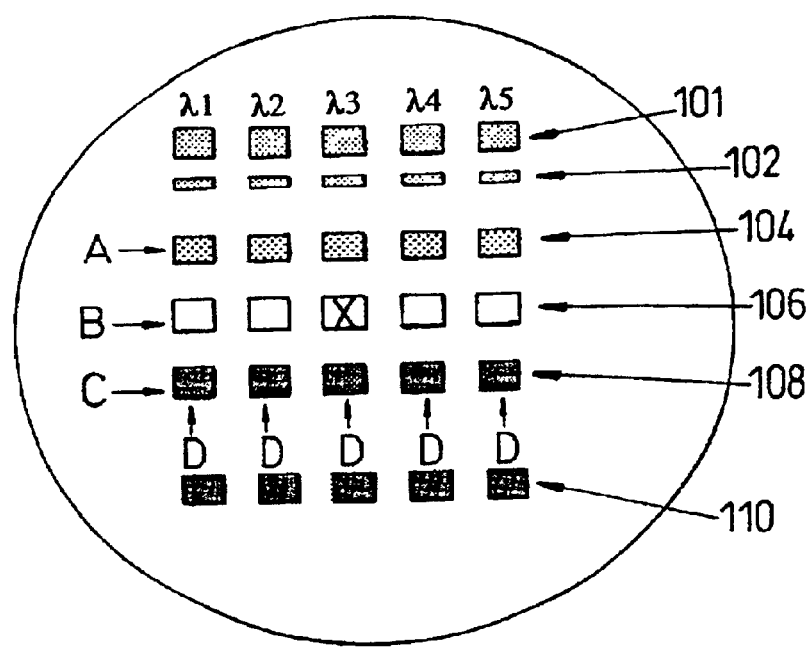
FIG. 8 shows a micro-analysis array of micro-tubes according to the present invention arranged on a wafer of material.

The arrangement shown in FIG. 8 shows an array of micro-analysis systems shown in FIG. 9. A bank of five LED's 101 is provided, each outputting light at a specific wavelength which in this case is different for each of the five LEDs ($\lambda_1 - \lambda_5$). Optical filters 102 are provided for each of the LEDs to further ensure the light emitted has the correct properties. It should be noted that it would also be possible to arrange for the LED's to be similar and to emit a broad spectrum of wavelengths and each filter 102 to transmit a narrow wavelength range.

A number of banks of cuvettes 104, 106, 108, in this case three, are provided to contain reagents of interest and a bank of detectors 110 are provided to measure the amount of light transmitted through the system.

Two starting materials for a particular reaction are held in the banks of micro-tubes 104, 108. Each of the starting materials can be moved into the bank of cuvettes 106 using a transport system fabricated onto the wafer (which is not shown). Because the light sources are emitting light at a range of wavelengths a reaction can be rapidly screened to see if it is producing the desired product. The product would have a specific absorption profile at the different wavelengths $\lambda_1 - \lambda_5$ and could therefore be quickly screened for. By having a plurality of reagents in a plurality of reservoirs available to be transported in the cuvettes, 106, a whole series of reactions can be rapidly screened.

Figure 10:
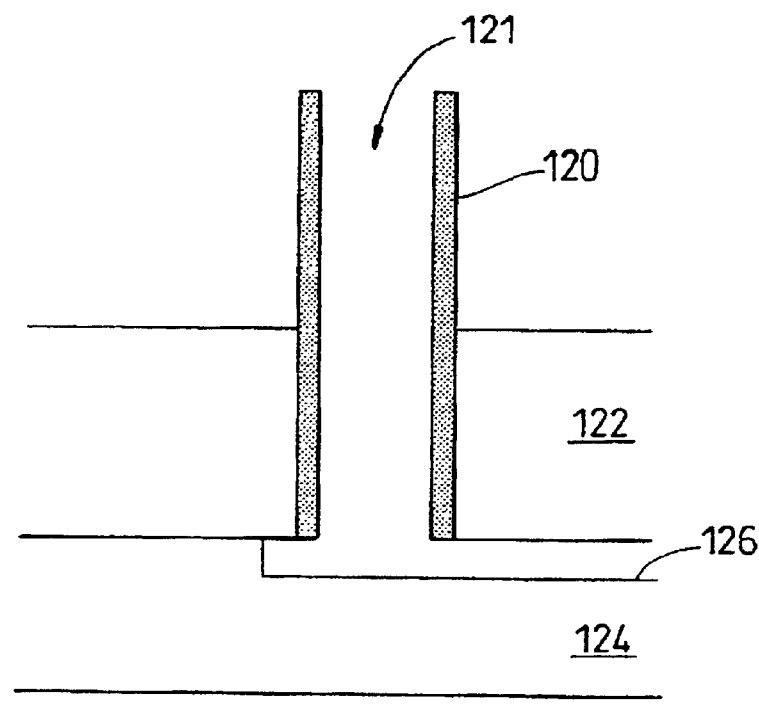
FIG. 10 shows a cross section through a micro-manipulation system according to the present invention.

A further example of how the micro-projection (or micro-tube) of FIG. 6 may be used is shown in FIG. 10. An $SiO_2$ micro-projection 120 is provided on a first silicon wafer 122 using the processes as described in relation to FIG. 4. It is ensured that the duct 121 passes entirely through the first silicon wafer 122. This can be achieved by ensuring that the duct 121 passes through the wafer 122 or could be achieved by removing material from the underside of the wafer 122.

A second silicon wafer 124 having a channel 126 etched in its upper surface is attached to the lower side of the first silicon wafer 122 so that the channel 126 communicates with the duct 121. The second wafer 124 can be attached to the first using, for example, adhesive or wafer bonding.

This apparatus can be used as a micro-manipulation system and used to pick up small objects. A vacuum pump (not shown) can be connected to the channel 126 so that small objects placed against the end portion of the micro-projection 120 can be picked up by applying a vacuum to the channel 126 and duct 121.

It may also be possible to provide control electronics on the silicon wafer 124. The vacuum pump could be provided externally of the wafer 122 or it may be possible to provide a silicon micro-pump using micro-machining techniques.

Further uses of the barbs of FIGS. 6 and 7 could be in the field of transdermal skin patches or transdermal drug delivery systems. For such uses a circular cross section micro-projection with a portion removed as in FIG. 7 may be preferable owing to the bevelled end portion which would be produced. Further, a second wafer may be attached to the rear of the wafer onto which the barb has been fabricated to provide a channel through which material can be delivered. If the needles are made of conducting material, then an electrical potential could be applied to them.

The micro-projections of FIGS. 6 and 7 could also be made to match the shape and dimensions of the optic fibres. The skilled person will appreciate that optical fibres have a circular cross section and that the micro-projections of FIGS. 6 and 7 would also need to have a circular cross section. Coupling between fibres and a silicon wafer could be achieved by inserting the fibre into the duct of the micro-projections. The skilled person will appreciate that this is different from conventional coupling in that the fibre is normal to the surface rather that orthogonal to it. It may be necessary to provide some device (perhaps a mirror) to reflect the light into the plane of the wafer.

Figure 11:
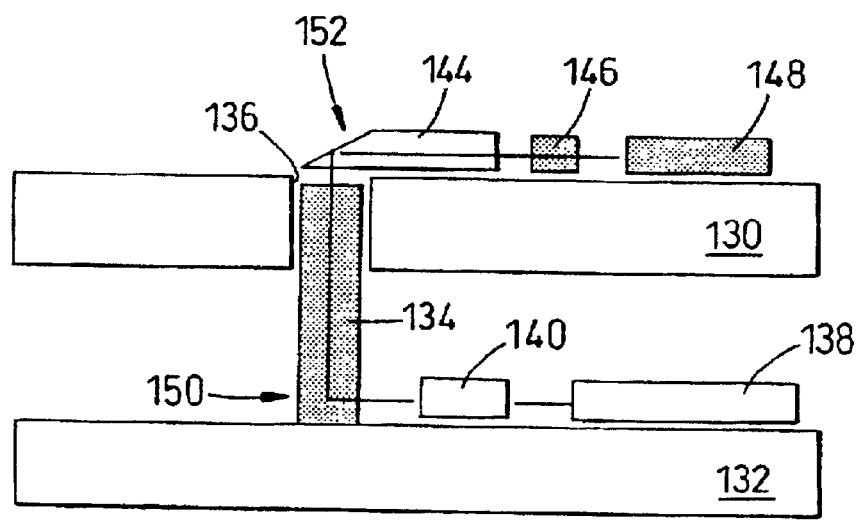
FIG. 11 shows a cross section through two wafers of material which are optically linked using the methods of the present invention.

An extension of the fibre optic coupler idea can be seen in FIG. 11 wherein a second silicon wafer 130 has been coupled to a first silicon wafer 132 on which a micro-projection (or micro-tube) 134 has been formed according to the processes described in relation to FIG. 4. A hole 136 is created through the second wafer 130 which is large enough to receive the micro-projection 134.

The skilled person will appreciate that the micro-projection 134 could be solid or hollow as described in relation to FIG. 4.

Processing electronics 138 could be formed onto the first wafer (or mounted onto it) which control a laser 140. The output of the laser 140 is directed toward the micro-projection 134. A waveguide 144 guides light travelling up the barb 134 to a photodetector 146 which receives the light and converts it into a signal to be transmitted to a second electronic device 148.

A direction means is provided in a bottom region 150 of the micro-projection 134 to ensure that light incident upon the duct from the laser 140 is directed along the micro-projection 134. The waveguide 144 has an portion 152 which acts to direct light incident upon it along the waveguide 144 to the photodetector 146.

The direction means may be a roughening of the inside of the tube, or may be an inverse of the end portion of the waveguide structure 144. The skilled person will appreciate that other means may be possible for realising the direction means.

In use, a signal is output from the laser 140. The light from the laser 140 travels to the micro-projection 134 and is directed up through the barb 134 by the direction means. An electrical signal is input to the second electrical device 148 as a result of the optical signal being passed along the waveguide 144 and being converted to an electrical signal by the photodetector 146.

Such a scheme may be advantageous in that the light does not travel in free space and is therefore not susceptible to interference from airborne particles. The skilled person will realise that the positioning of the waveguides, etc. could be arranged so that the light does not have to pass through free space.

Figure 12:
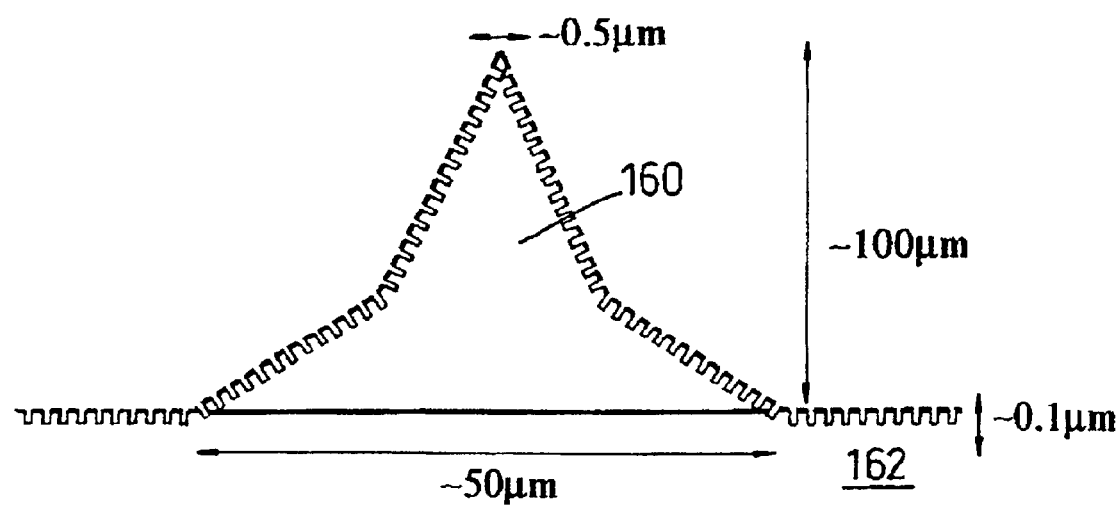
FIG. 12 shows a cross section through an alternative embodiment of a micro-projection with a porosified surface.

FIG. 12 shows a micro-barb 160 which has been fabricated onto the surface of a silicon wafer 162. The surface of the barb has been porosified. As disclosed in WO 96/10630 it is possible to produce barbs onto the surface of a silicon wafer. However, porosifying the surface provides barbs primarily of bulk silicon with a porous coating which enables substances to be immobilised onto the surface of the barb. The barb may or may not have a duct through the centre portion.

The porosified coating could be formed by either an electrochemical anodisation process or possibly by immersing the structure into a stain solution such as a mixture of hydrofluoric acid and nitric acid.

Figure 13:
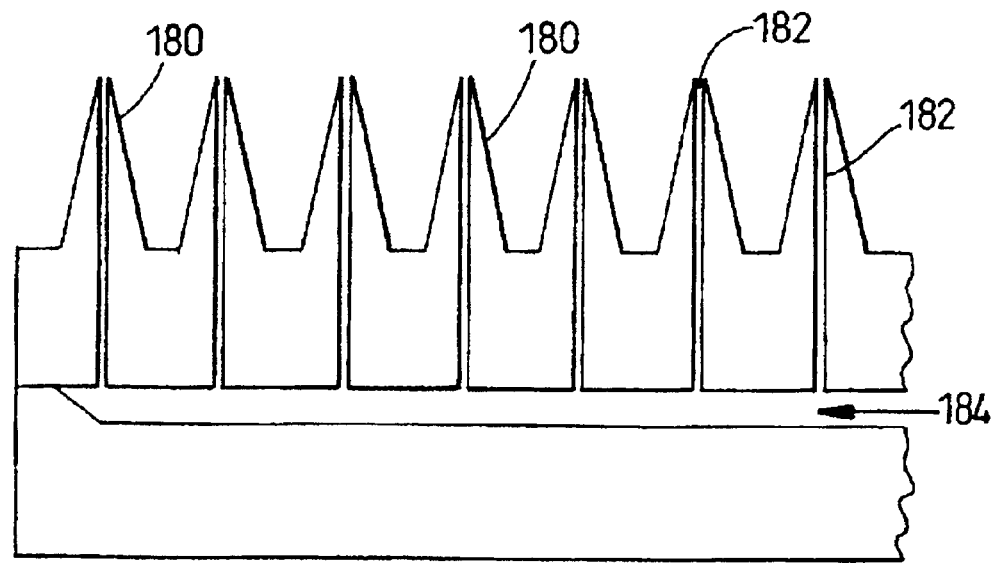
FIG. 13 shows a cross section through an array of micro-projections.

FIG. 13 shows an array of micro-barbs (or micro-projections) 180 each with a duct 182 along a centre portion connected to a channel 184. These barbs 180 can be fabricated according to the techniques described in relation to FIGS. 1 to 3.

The micro-barb array could be used to inject substances, for example transdermally, from a reservoir connected to the channel 184.

Throughout this specification reference is made to a micro-projection having a duct. The micro-projection can be fabricated from a first material (which may be the same as the material upon which the micro-projection is fabricated) or from a second material (which may be different from the material upon which the micro-projection is fabricated). It should be noted that in embodiments wherein the micro-projection is fabricated from a second material that the duct may be filled with the second material (or may be filled with a third material different from the second material). As such, the micro-projection may be a solid rod which may be fabricated from a single material. Such a solid micro-projection may still be used as a waveguide.

What is claimed is:

1. A method of providing a silicon micro-needle, the micro-needle having a base adjoining a silicon substrate, a tip remote from said base, and a duct passing from said base to said tip, the method comprising:
   a. providing a duct in said silicon substrate; and subsequently
   b. selectively removing the substrate from around the duct to provide a micro-needle coincident with the duct.

2. A method according to claim 1 wherein a mask is lithographically provided on a substrate of the first material prior to the formation of the duct.

3. A method according to claim 2 wherein the mask is used to provide the duct which is fabricated by any one of the following techniques: plasma enhanced etching, laser ablation, light assisted anodisation, ion beam milling, focused ion beam milling.

4. A method according to claim 1 wherein the micro-needle is bounded by planes of the first material which have a low etch rate.

5. A method according to claim 4 wherein an anisotropic etch is used to selectively remove the first material.

6. A method according to claim 1 wherein the first material is removed by any one of the following methods: focused ion beam milling, etching combined with a domed resist mask.

7. A method according to claim 1 wherein the method is arranged to provide a micro-needle whose outer walls are inclined to a plane that is perpendicular to the substrate to which the micro-needles are adjacent.

8. A method according to claim 1 in which once the micro-needle has been created the method further includes linking the duct to a reservoir.

9. A method according to claim 8 in which a portion of the first material is removed from a side opposite a side of the first material where the micro-needle has been fabricated.

10. A method according to claim 8 in which the first material is attached to a second piece of material.

11. A method according to claim 10 in which the second piece of material has a channel which connects to the duct and links the duct to a reservoir.

12. A method according to claim 10 in which the first material has a channel which connects to the duct and links the duct to a reservoir.

13. A method according to claim 10 in which the two pieces of material are fabricated from same material.

14. A method according to claim 1 in which the micro-projection is fabricated substantially normal to the surface of the first material.

15. A method according to claim 1 wherein a surface region of the micro-needle is porosified after the needle has been fabricated.

16. A method according to claim 15 wherein the porosification is provided by one of the following techniques: electrochemical anodisation, or immersing the structure is a stain etching solution.

17. A method of providing a silicon micro-needle, the micro-needle having a base adjoining a silicon substrate, a tip remote from said base, and a duct passing from said base to said tip, the method comprising:
   a. selectively removing the silicon substrate to provide a micro-needle; and subsequently
   b. providing a duct coincident with the micro-needle.

18. A method according to claim 17 wherein the micro-needle is bounded by planes of the first material which have a low etch rate.

19. A method according to claim 18 wherein an anisotropic etch is used to selectively remove the first material.

20. A method according to claim 17 wherein said micro-needle is formed by any one of the following techniques: focused ion beam milling, etching combined with a domed resist mask.

21. A method according to claim 17 wherein once the micro-needle has been formed a planar surface is provide covering the micro-needle.

22. A method according to claim 21 wherein the duct is provided by lithographic processes performed on the planar surface.

23. A method according to claim 22 wherein once the duct has been provided the planar surface is removed.

24. A method of providing a micro-needle on the surface of a first material, the micro-needle having a base adjoining the first material, a tip remote from said base, and a duct passing from said base to said tip, the method comprising:
   a. providing a duct in said first material,
   b. lining said duct with a second material, and
   c. removing said first material from around said second material leaving a micro-needle fabricated from said second material attached to said first material and upstanding therefrom.

25. A method according to claim 24, wherein the second material is any one of the following materials: $SiO_2$, a metal, ceramic, a polymer, a semi-conductor.

26. A method according to claim 24 wherein a portion of the second material covering the inside surface of the duct is removed before or whilst the first material is removed from around the second material.

27. A method according to claim 24 wherein the first material is removed by etching.

28. A method according to claim 24 wherein a mask is lithographically provided on a substrate of the first material prior to the formation of the duct.

29. A method according to claim 28 wherein the mask is subsequently u used to control fabrication of the duct.

30. A method according to claim 24 wherein the duct is fabricated using any one of the following processes: plasma based etching, laser ablation, focused ion beam milling, light assisted anodisation of silicon.

31. A method according to claim 24 wherein the second material is provided by any one of the following processes: oxidiation, deposition.

32. A method according to claim 24 wherein the microneedle is shaped by removing a portion of the second material.

* * * * *